United States Patent [19]

Ehr

[11] 4,427,695
[45] Jan. 24, 1984

[54] COMPOSITIONS OF ASYMMETRIC DIPHENYL ORGANOTINS AND USE FOR CONTROL OF PLANT DISEASES

[75] Inventor: Robert J. Ehr, Pittsburg, Pa.

[73] Assignee: The Dow Chemical Company, Midland, Mich.

[21] Appl. No.: 405,474

[22] Filed: Aug. 5, 1982

Related U.S. Application Data

[63] Continuation of Ser. No. 270,423, Jun. 4, 1981, abandoned, which is a continuation-in-part of Ser. No. 195,277, Oct. 8, 1980, abandoned.

[51] Int. Cl.$^3$ ............................................. A01N 55/04
[52] U.S. Cl. .................................................... 424/288
[58] Field of Search ........................................ 424/288

[56] References Cited

U.S. PATENT DOCUMENTS 3,435,118  3/1969  Ligett ................................ 424/288

FOREIGN PATENT DOCUMENTS 797073  6/1958  United Kingdom ................ 424/288

OTHER PUBLICATIONS

Ingham et al., *Chemical Reviews,* 60, 482, 483, 500, 522 (1960).

*Primary Examiner*—Delbert R. Phillips
*Assistant Examiner*—F. T. Moezie

[57] ABSTRACT

Compositions comprising asymmetric substituted diphenyl organotins such as (acetyloxy)bis-(3,4-dichlorophenyl)methylstannane and their use for controlling grape downy mildew.

14 Claims, No Drawings

COMPOSITIONS OF ASYMMETRIC DIPHENYL ORGANOTINS AND USE FOR CONTROL OF PLANT DISEASES

CROSS REFERENCE TO RELATED APPLICATION

This application is a continuation of Ser. No. 270,423, filed on June 4, 1981, now abandoned which in turn is a continuation-in-part of copending application Ser. No. 195,277, filed Oct. 8, 1980, now abandoned.

BACKGROUND OF THE INVENTION

U.S. Pat. No. 2,922,738 relates to organotin salts containing 2 or 3 organo groups directly attached to tin and to fungicidal compositions characterized by an essential lack of phytotoxicity. British Pat. No. 1,232,691 relates to certain unsymmetrical organotin halides and teaches that they may find use as fungicides or as catalysts for polyurethanes. U.S. Pat. No. 3,471,539 and Japanese Patent Appln. No. 13261/65 teach methods for making substituted triorganotin halides.

SUMMARY OF THE INVENTION

In accordance with the present invention grape downy mildew is controlled by a method which comprises applying at least a fungicidally effective amount but less than a phytotoxic amount to said grape plants of an organotin compound of the following formula:

wherein:
each X is independently halogen, $C_1$–$C_4$ alkyl, haloalkyl, —$OCH_3$ or —$SCH_3$;
n is 0, 1 or 2;
Y is straight or branched chain $C_1$–$C_{12}$ alkyl, $C_3$–$C_7$ cycloalkyl, $C_3$–$C_8$ carboalkoxyalkyl, cyanoalkyl, hydroxyalkyl, alkylamido or lower alkylphenyl, the lower alkyl in each having 1 to 4 carbon atoms; and
Z is halogen, hydroxide, $O/2$, lower alkanoate or tosylate.

The invention further provides a fungicidal composition which comprises a non-phytotoxic agricultural carrier and at least a fungicidally effective amount of an organotin compound of the formula:

wherein:
each X is independently halogen $C_1$–$C_4$ alkyl, haloalkyl, —$OCH_3$ or —$SCH_3$;
n is 0, 1 or 2;
Y is straight or branched chain $C_1$–$C_{12}$ alkyl, $C_3$–$C_7$ cycloalkyl, $C_3$–$C_8$ carboalkoxyalkyl, cyanoalkyl, hydroxyalkyl, alkylamido or lower alkylphenyl, the lower alkyl in each having 1 to 4 carbon atoms; and
Z is halogen, hydroxide, $O/2$, lower alkanoate or tosylate.

DETAILED DESCRIPTION OF THE INVENTION

It has been found that the present organotin compositions are particularly adapted to be employed for the control of grape downy mildew (*Plasmopara viticola*). Some compounds in this family also possess systemic and curative properties. Many of these compositions are unique because of the extremely low levels of chemical required to control grape downy mildew.

These chemicals may be prepared as dusts, wettable powders, flowable concentrates, or emulsifiable concentrates.

The invention includes within its scope a method for the control of grape downy mildew attacking plants or plant parts which method comprises applying to the plants, the plant parts or to the organisms or to their habitats one or more of the compositions in accordance with the invention.

It is an advantage of the present invention that these compositions can be applied to growing vegetation in amounts required for effective control of grape downy mildew without significant injury to the plants. It is a further advantage that the preferred embodiments of the present invention are of low toxicity to mammals. It is another advantage that a single application of the compositions can provide a residual and extended control of grape downy mildew over a period of several months. Also, the compounds can be effective in eliminating established grape downy mildew infestation. Furthermore, some compounds have been found to be translocated in plants and thus can provide a systemic protection against grape downy mildew.

The method of the present invention comprises contacting grape plants with a fungicidal amount of one or more of the compounds. However, the present invention also embraces the employment of a liquid, powder, dust or granular composition containing one or more of the compounds and one or more additives including organic solvents, petroleum distillates, water or other liquid carriers, surface active dispersing agents, and finely divided inert solids. In such compositions, the active ingredients oftentimes are present in a concentration from about 2 percent to about 95 percent by weight preferably 10 percent to about 95 percent by weight and most advantageously 10 percent to about 60 percent by weight. When employed in the form of diluted flowable compositions or a wettable powder composition containing 2 to 10,000 ppm of organotin compound, preferably 10 to 600 ppm are employed. When the carrier contains a surface active agent, from about 0.1 to about 20 percent by weight of the active ingredient is advantageously employed. Depending upon the concentration in the composition, such augmented compositions are adapted to be employed for the control of the undesirable fungi or employed as concentrates and subsequently diluted with additional inert carrier. e.g. water, to produce the ultimate treating compositions. In general, good results can be obtained with liquid compositions containing from about 0.0001 to about 2.0 percent by weight of the toxicant in the final diluted form. With dusts, good results can usually be obtained with compositions containing from about 0.001 to about 2.0 percent or more by weight of toxicant. Where the compositions are to be applied to living plants, it is preferred that the toxicant be present in an amount not to exceed about 0.8 percent in liquid compositions and about 1.0 percent in dusts. In terms of acreage application, good controls of grape downy mildew can be obtained when the active ingredients are applied to growing plants at a dosage of from about 0.004 to about 3 or more pounds per acre (0.0045 to 3.36 kg/hectare).

In the preparation of dust, or wettable powder compositions, the toxicant products can be compounded with any of the finely divided solids, such as prophyllite, talc, chalk, gypsum, fuller's earth, bentonite, attapulgite, starch, casein, gluten, or the like. In such operations, the finely divided carrier is ground or mixed with the toxicant or wet with a solution of the toxicant in a volatile organic solvent. Also, such compositions when employed as concentrates can be dispersed in water, with or without the aid of dispersing agents to form spray mixtures.

Granular formulations are usually prepared by impregnating a solution of the toxicant in a volatile organic solvent onto a bed of coarsely divided attapulgite, bentonite, diatomite, or the like.

Similarly, the toxicant products can be compounded with a suitable water-immiscible inert organic liquid and a surface active dispersing agent to produce an emulsifiable concentrate which can be further diluted with water and oil to form spray mixtures in the form of oil-in-water emulsions. In such compositions, the carrier comprises an aqueous emulsion, i.e., a mixture of inert water-immiscible solvent, emulsifying agent, and water. Preferred dispersing agents which can be employed in these compositions, are oil-soluble materials including non-ionic emulsifiers such as the condensation products of alkylene oxides with the inorganic aids, polyoxyethylene derivatives or sorbitan esters, complex ether alcohols, and the like. Also, oil-soluble ionic emulsifying agents such as mahogany soaps can be used. Suitable inert organic liquids which can be employed in the compositions include petroleum oils and distillates, toluene, liquid halohydrocarbons, and synthetic organic oils. The surface-active dispersing agents are usually employed in liquid compositions and in the amount of from 0.1 to 20 percent by weight of the combined weight of the dispersing agent and active compound.

The invention is further illustrated by the following examples.

EXAMPLE 1

Concentrates, 10,000-ppm, of (acetyloxy)bis-(3,4-dichlorophenyl)methylstannane (Cpd A) and of (acetyloxy)bis-(4-bromophenyl)methylstannane (Cpd B) were prepared in acetone. 0.9 ml of these concentrates were individually injected into 29.1 ml of an aqueous spray solution (water: isopropanol (80:20) mixture) containing 250 ppm Triton X-155 to form 300-ppm solutions. Appropriate aliquots of the 300-ppm solutions were diluted with spray solution to form 75 and 19-ppm solutions. Similar dilution series were prepared for chlorothalonil (tetrachloroisophthalonitrile) and fentin hydroxide (hydroxytriphenylstannane). The 10,000-ppm concentrate of chlorothalonil was prepared in water from the 75% wettable powder commercial formulation. The 10,000-ppm concentrate of fentin hydroxide was prepared in isopropanol.

Spray solutions of each chemical at each concentration were individually and separately applied with a hand sprayer to thoroughly cover the foliage of 1-month-old grape seedlings (var. Carignane). The treated plants were held in a greenhouse. Two days after treatment, the plants were covered and placed overnight once in a bioclimatic chamber at 64° F. and 100% relative humidity (R.H.). Four days after treatment, the seedlings were inoculated with freshly harvested sporangia of the downy mildew fungus, *Plasmopara viticola*, at a concentration of approximately $10^5$ sporangia/ml by spraying with a hand sprayer. The plants were then covered and held in a bioclimatic chamber at 64° F. and 100% R.H. for 3 days, after which they were returned to a greenhouse.

After 2 days in the greenhouse, the plants were inoculated a second time as previously described. Following 3 days in a bioclimatic chamber, the results of the first inoculation were assessed. Percent control of disease on both the foliage present at the time of treatment and that which emerged following treatment were rated. After an additional 2 days in a greenhouse and 3 days in a bioclimatic chamber, the percent control of disease was assessed as above for the second innoculation.

| | | PERCENT CONTROL OF GRAPE DOWNY MILDEW | | | | | |
|---|---|---|---|---|---|---|---|
| | | Foliage Present at Treatment | | | Foliage Emergent after Treatment | | |
| Treatment | Innoculation | Concentration, ppm | | | | | |
| | | 300 | 75 | 19 | 300 | 75 | 19 |
| Cpd A | First | 99 | 95 | 93 | 100 | 97 | 60 |
| | Second | 98 | 90 | 75 | 99 | 75 | 25 |
| Cpd B | First | 100 | 100 | 98 | 100 VSP | 100 | 99 |
| | Second | 100 | 100 | 95 | 97 VPS | 95 | 60 |
| Chlorothalonil | First | 93 | 75 | 0 | 90 | 60 | 0 |
| | Second | 50 | 50 | 0 | 35 | 25 | 0 |
| Fentin hydroxide | First | TP | 97 SP | 97 | TP | 100 SP | 60 |
| | Second | TP | 97 MP | 97 | TP | 75 SP | 25 |

Notations:
TP = Plants killed from phytotoxicity.
MP = Moderate phytotoxicity.
SP = Slight phytotoxicity.
VSP = Very slight phytotoxicity.

EXAMPLE 2

10,000-ppm Concentrates of Cpd A and fentin hydroxide were prepared and diluted with spray solution to 300, 75 and 19 ppm as in Example 1. A 10,000-ppm concentrate of maneb (manganese salt of ethylenebisdithiocarbamic acid) was prepared in water from an 80% wettable powder commercial formulation and diluted with spray solution to concentrations of 300, 75 and 19 ppm.

A repeat application test was initiated when grape seedlings (var. Carignane) were in the 4- to 6-leaf stage of growth. Spray solutions at each concentration of each chemical were applied to grape seedlings as in Example 1 but at weekly intervals for 3 weeks. The plants were inoculated 4 days after treatment according to the methods of Example 1. Between each successive treatment and inoculation, the plants were covered and placed overnight in a bioclimatic chamber held at 64° F. and 100% R.H. The final disease control assessments were made one week after the final inoculation.

| PERCENT CONTROL OF GRAPE DOWNY MILDEW | | | |
|---|---|---|---|
| | Concentration, ppm | | |
| Treatment | 300 | 75 | 19 |
| Cpd A | 100 | 91 | 72 |
| Fentin hydroxide | 100 TP | 100 MP | 93 SP |

PERCENT CONTROL OF GRAPE DOWNY MILDEW

| | Concentration, ppm | | |
|---|---|---|---|
| Treatment | 300 | 75 | 19 |
| maneb | 57 | 19 | 0 |

Notations:
TP = Plants killed from phytotoxicity.
MP = Moderate phytotoxicity.
SP = Slight phytotoxicity.

Following the above procedures and employing spray solutions containing 75 ppm active ingredient of various compounds within the scope of the present invention the following results were obtained:

| Compound | % Control Grape Downy Mildew |
|---|---|
| (Tosyloxy)-bis-(4-chlorophenyl)-n-butylstannane | 87 |
| (Acetyloxy)-bis-(4-chlorophenyl)-cyclohexylstannane | 83 |
| (Acetyloxy)-bis-(4-chlorophenyl)-n-butylstannane | 100 |
| (Bromo)-bis-(4-chlorophenyl)-n-butylstannane | 100 |

Following the above procedures and employing spray solutions containing 300 ppm active ingredient of various compounds within the scope of the present invention, the following results were obtained:

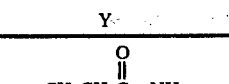

| X | Y | Z | % Control Grape Downy Mildew |
|---|---|---|---|
| 4-Cl | n-butyl | bis O | 98 |
| 4-Cl | t-butyl | bis O | 96 |
| 3-$CH_3$ | methyl | Br | 100 |
| 3-$CH_3$ | methyl | OH | 100 |
| 3-$CH_3$ | methyl | acetate | 100 |
| 4-Cl | cyclohexyl | bis O | 100 |
| 2-$OCH_3$ | methyl | Br | 88 |
| 3-$CH_3$ | cyclohexyl | OH | 95 |
| 3-$CH_3$ | n-butyl | acetate | 100 |
| 3-$CH_3$ | cyclohexyl | acetate | 87 |
| 4-$OCH_3$ | methyl | Br | 100 |
| 4-Cl | $CH_2CH_2\overset{O}{\overset{\|}{C}}OC_2H_5$ | Br | 100 |
| 4-$OCH_3$ | methyl | acetate | 100 |
| 3-$CF_3$ | n-butyl | OH | 86 |
| 3-$CF_3$ | n-butyl | acetate | 93 |
| 4-$CF_3$ | n-butyl | acetate | 98 |
| 4-$CH_3$ | n-butyl | acetate | 100 |
| 4-Cl | —$CH_2C(CH_3)_2\phi$ | Br | 80 |
| 4-Cl | —$CH_2C(CH_3)_2\phi$ | acetate | 88 |
| 4-Cl | —$CH_2CH_2\overset{O}{\overset{\|}{C}}OC_2H_5$ | tosylate | 100 |
| 4-t-butyl | n-butyl | Br | 59 |
| 4-$CH_3$ | n-butyl | tosylate | 100 |
| 4-Cl | —$CH_2C(CH_3)_2\phi$ | tosylate | 62 |
| 4-t-butyl | n-butyl | tosylate | 59 |
| 4-$SCH_3$ | n-butyl | acetate | 100 |
| H | —$CH_2CH_2C\equiv N$ | Cl | 90 |
| H | —$CH_2CH_2OH$ | Br | 75 |

EXAMPLE 3

Stratified grape seed (var. Carignane) were sown in trays of vermiculite and the emerging seedlings were transplanted into 2-inch plastic pots of vermiculite. Two to 3 weeks later, plants were selected with a young and succulent, but fully expanded leaf. Except for this leaf, all others were excised. The underside of the leaf was sprayed to runoff with a 100-ppm suspension of the chemical. After the plants dried, the experiment was moved into the greenhouse for 2 days. The plants were then inoculated by spraying the leaf's underside with a brief burst of spray containing freshly collected sporangia of *Plasmopara viticola* at $10^5$ propagules/ml. Following incubation, the experiment was placed in the greenhouse for 2 days, during which a light yellow mosaic pattern developed on untreated checks. The plants were returned to the bioclimatic chamber for 2 days and percent control, based on sporulation, were evaluated. The following result was obtained.

| X | Y | Z | % Control Grape Downy Mildew |
|---|---|---|---|
| H | —$CH_2CH_2\overset{O}{\overset{\|}{C}}$—$NH_2$ | Br | 75 |

When applied at dosage levels of from about 10 to about 5000 parts per million, each of the compounds of the present invention, the utility of which is not specifically recited above, has the ability to kill, inhibit or otherwise control grape downy mildew.

I claim:

1. The method of controlling grape downy mildew which comprises applying at least a fungicidally effective amount but less than a phytotoxic amount to said grape plants of an organotin compound of the following formula:

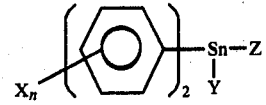

wherein:
each X is independently halogen, $C_1$-$C_4$ alkyl, haloalkyl, —$OCH_3$ or —$SCH_3$;
n is 0, 1 or 2;
Y is straight or branched chain $C_1$-$C_{12}$ alkyl, $C_3$-$C_7$ cycloalkyl, $C_3$-$C_8$ carboalkoxyalkyl, cyanoalkyl, hydroxyalkyl, alkylamido or lower alkylphenyl, the lower alkyl in each having 1 to 4 carbon atoms; and
Z is halogen, hydroxide, O/2, lower alkanoate or tosylate.

2. The method as in claim 1 wherein the organotin compound is formulated with a non-phytotoxic agricultural carrier and is applied at a concentration in the range of 2 ppm up to the phytotoxic concentration of the organotin compound.

3. The method as in claim 2 wherein the organotin compound is applied in a concentration in the range of 10 ppm to 600 ppm but below the phytotoxic concentration.

4. A composition for control of grape downy mildew which comprises a non-phytotoxic agricultural carrier and at least a fungicidally effective amount of an organotin compound of the formula:

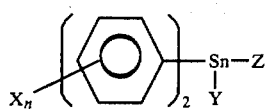

wherein:
each X is independently halogen, $C_1$-$C_4$ alkyl, haloalkyl, —$OCH_3$ or —$SCH_3$;
n is 1 or 2;
Y is straight or branched chain $C_1$-$C_{12}$ alkyl, $C_3$-$C_7$ cycloalkyl, $C_3$-$C_8$ carboalkoxyalkyl, cyanoalkyl, hydroxyalkyl, alkylamido or lower alkylphenyl, the lower alkyl in each having 1 to 4 carbon atoms; and
Z is halogen, hydroxide, O/2, lower alkanoate or tosylate.

5. The composition as in claim 4 in the form of an emulsion concentrate, a flowable concentrate, a wettable powder or a granulated composition.

6. The composition as in claim 5 which contains from about 2 percent to about 95 percent by weight of the organotin compound.

7. The composition as in claim 6 which contains from about 10 percent to about 60 percent by weight of the organotin compound.

8. The composition as in claim 5 in the form of a flowable composition or a wettable powder.

9. The composition as in claim 8 which contains from about 2 to about 10,000 ppm of the organotin compound.

10. The composition as in claim 9 which contains from about 10 to about 600 ppm of the organotin compound.

11. The composition as in claim 4 in which X is Cl or Br.

12. The composition as in claim 4 in which Y is $C_1$-$C_{10}$ alkyl or $C_3$-$C_7$ cycloalkyl.

13. The composition as in claim 4 wherein Z is Cl, Br, OH, O/2 or acetate.

14. The composition as in claim 4 wherein X is Cl or Br, Y is methyl and Z is halogen, hydroxide, O/2, or acetate.

* * * * *

UNITED STATES PATENT AND TRADEMARK OFFICE
CERTIFICATE OF CORRECTION

PATENT NO. : 4,427,695

DATED : January 24, 1984

INVENTOR(S) : Robert J. Ehr

It is certified that error appears in the above—identified patent and that said Letters Patent is hereby corrected as shown below:

Col. 2, line 59, delete "carrier. e.g." and insert --carrier, e.g.--.

Col. 4, line 30, delete "VPS" and insert --VSP--.

Col. 6, line 19, delete "were" and insert --was--; line 50, delete "0, 1 or 2" and insert --1 or 2--.

Signed and Sealed this

Tenth Day of July 1984

[SEAL]

Attest:

GERALD J. MOSSINGHOFF

Attesting Officer     Commissioner of Patents and Trademarks